(12) United States Patent
Fitzgerald et al.

(10) Patent No.: US 9,102,593 B2
(45) Date of Patent: Aug. 11, 2015

(54) PROCESS FOR THE PREPARATION OF RETIGABINE

(75) Inventors: Russ N. Fitzgerald, Research Triangle Park, NC (US); Alan Millar, Research Triangle Park, NC (US); Jennifer Fell Toczko, Research Triangle Park, NC (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/980,210

(22) PCT Filed: Jan. 16, 2012

(86) PCT No.: PCT/EP2012/050559
§ 371 (c)(1),
(2), (4) Date: Jul. 17, 2013

(87) PCT Pub. No.: WO2012/098075
PCT Pub. Date: Jul. 26, 2012

(65) Prior Publication Data
US 2013/0345465 A1    Dec. 26, 2013

Related U.S. Application Data

(60) Provisional application No. 61/509,802, filed on Jul. 20, 2011.

(51) Int. Cl.
*C07C 205/00* (2006.01)
*C07C 269/06* (2006.01)
*C07C 269/04* (2006.01)

(52) U.S. Cl.
CPC ............. *C07C 269/06* (2013.01); *C07C 269/04* (2013.01)

(58) Field of Classification Search
CPC .......................... C07C 271/28; C07C 269/04
USPC ........................................ 560/21, 27
See application file for complete search history.

(56) References Cited

U.S. PATENT DOCUMENTS 5,384,330 A * 1/1995 Dieter et al. .................. 514/535
5,463,109 A * 10/1995 Nishihira et al. ............. 560/157

FOREIGN PATENT DOCUMENTS

| EP | 2230228 A1 | | 9/2010 |
|---|---|---|---|
| WO | WO2009/034308 | * | 3/2009 |
| WO | WO 2011089126 | * | 1/2011 |
| WO | 2011012659 A2 | | 2/2011 |
| WO | 2011089126 A2 | | 7/2011 |
| WO | 2011101456 A2 | | 8/2011 |

OTHER PUBLICATIONS

McHale (E2 Elimination, 2008).*
Carloni et al.; "Catalytic Activity of MCM-41-TBD in the Selective Preparation of Carbamates and Unsymmetrical Alkyl Carbonates from Diethyl Carbonate" (XP002676331); Journal of Catalysis; 2002; vol. 205, No. 1; pp. 199-204.

* cited by examiner

*Primary Examiner* — Yevegeny Valenrod
*Assistant Examiner* — Blaine G Doletski
(74) *Attorney, Agent, or Firm* — Kathryn L. Coulter

(57) ABSTRACT

This invention relates to a novel chemical process for the synthesis of 2-ethyoxycarbonylamino-5-(4-fluorobenzylamino)-nitrobenzene and its use in the preparation of 2-amino-4-(4-fluorobenzylamino)-1-ethoxycarbonylaminobenzene (retigabine/ezogabine) and its polymorphic forms thereof.

20 Claims, No Drawings

PROCESS FOR THE PREPARATION OF RETIGABINE

This application is filed pursuant to 35 U.S.C. §371 as a United States National Phase Application of International Patent Application No. PCT/EP2012/050559 filed Jan. 16, 2012, which claims priority from International Patent Application No. PCT/EP2011/050633 filed Jan. 18, 2011 and U.S. Provisional Application No. 61/509,802 filed on Jul. 20, 2011.

This invention relates to a novel chemical process for the synthesis of 2-ethyoxycarbonylamino-5-(4-fluorobenzylamino)-nitrobenzene and its use in the preparation of 2-amino-4-(4-fluorobenzylamino)-1-ethoxycarbonylaminobenzene (retigabine/ezogabine) and its polymorphic forms thereof.

BACKGROUND

2-Amino-4-(4-fluorobenzylamino)-1-ethoxycarbonylaminobenzene (which is known by the INN name retigabine, or its USAN name ezogabine) is disclosed in U.S. Pat. No. 5,384,330 and EP 0554 543. U.S. Pat. No. 5,384,330 discloses compounds which, can for example, be used as anti-epileptic, muscle-relaxing, fever-reducing and peripherally analgesically acting medications. Drugs of the future 1995 (2) 11:1112-1115 discloses a preparation of retigabine (D-23129). WO98/031663 (U.S. Pat. No. 6,538,151) discloses 3 different pure crystal modifications, called A, B and C. WO2010/009433 and US2010/0323016 disclose modified release formulations of retigabine. Marketing approval for retigabine as an adjunctive treatment of partial seizures has been granted in Europe and is currently being sought in the US, and other countries.

U.S. Pat. No. 5,384,330 describes two processes for making retigabine designated therein as Variant A and Variant B.

SUMMARY OF THE INVENTION

A novel, simplified and economic process has now been found for making 2-ethoxycarbonylamino-5-(4-fluorobenzylamino)-nitrobenzene. A further aspect of the invention is the preparation of retigabine using 2-ethoxycarbonylamino-5-(4-fluorobenzylamino)-nitrobenzene so made. Retigabine may then be optionally crystallised into one of its polymorphic forms.

In a first aspect of the invention there is therefore provided a process for the production of 2-ethoxycarbonylamino-5-(4-fluorobenzylamino)-nitrobenzene (a compound of formula (I)) or a salt thereof:

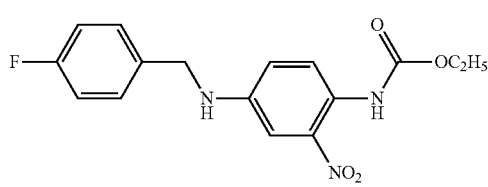

(I)

which comprises reacting 4-(4-fluorobenzylamino)-2-nitroaniline (the compound of formula (II))

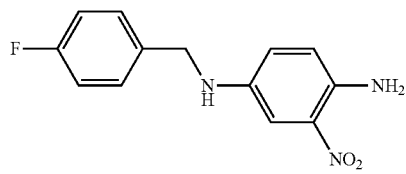

(II)

with diethylcarbonate in the presence of a base and optionally preparing a salt thereof.

The use of diethylcarbonate results in a more selective carbamylation of a compound of formula (II).

The term "base" is intended to mean any substance that can act as a proton acceptor. In one embodiment the base is a strong base. The bases may be selected from sodium ethoxide, sodium hydride, potassium tert-butoxide, n-butyl lithium, potassium hexamethyldisilylazide (KHMDS), cesium carbonate, potassium hydroxide, sodium pentoxide, sodium tert-butoxide, lithium ethoxide, sodium hydroxide, potassium ethoxide, diisopropyl ethyl amine (DIPEA), 1,8-diazabicylco[5.4.0]undec-7-ene (DBU), 1,4-diazabicyclo[2.2.2]octane (DABCO) or lithium tert-butoxide. In one embodiment the base is sodium ethoxide.

The Table lists the reaction parameters that provide optimal production of 2-ethoxycarbonylamino-5-(4-fluorobenzylamino)-nitrobenzene (a compound of formula (I)) or a salt thereof:

TABLE 1

Parameters and Limits for Reaction of 2-ethoxycarbonylamino-5-(4-fluorobenzylamino)-nitrobenzene with Diethylcarbonate in the presence of base

| Parameter | Low | High | Centerpoint/Normal Operating point |
| --- | --- | --- | --- |
| Equivalents NaOEt | 1.8 | 2.2 | 2.0 |
| Equivalents AcOH | 1.8 | 2.2 | 2.0 |
| Reaction Temperature (° C.) | 15 | 30 | 22.5 |
| Reaction Time(h) | 1.5 | 24 | 6 |

In one embodiment the base is present in range of 1.8 to 2.2 molar equivalents.

In one embodiment the base is neutralized with an acid. In one embodiment the acid is any organic or mineral acid. In one embodiment the acid is acetic acid. In one embodiment the acid is present in range of 1.8 to 2.2 molar equivalents.

In one embodiment diethylcarbonate is present in the range of 5 to 7 molar equivalents.

In one embodiment the reaction temperature is in the range 15 to 30° C.

In one embodiment the reaction time is in the range 1.5 to 24 hours.

The compound of formula (II) may be prepared by the reaction of 4-fluorobenzaldehyde and 4-amino-2-nitroaniline followed by reduction using standard procedures for example using NaBH$_4$ in solution in NaOH or n-methylpyrrolidine (NMP). Other common boron, aluminium or metal hydride reducing agents may be used.

A solvent used for the above reaction can be selected from an alcohol, for example ethanol or isopropanol (IPA). The alcohol may be denatured. The compound of formula (II) may be isolated in crystalline form by the addition of a counter solvent for example water.

It will be understood that the preparation of a compound of formula (II) involves the in situ preparation of 4-(4-fluorobenzylideneamino)-2-nitroaniline (compound of formula (III)

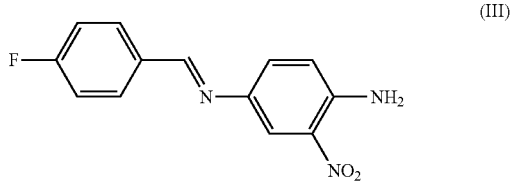 [SMILES: Nc1ccc(/N=C/c2ccc(F)cc2)cc1[N+](=O)[O-]]

Isolation of the compound of formula (III) is not necessary, although this is included in the scope of this invention. Judicious selection of the solvent for the first step of this reaction, IPA or ethanol, allows the processes to be carried out sequentially in the same vessel.

In a further embodiment of the present invention there is provided a process for the preparation of a compound of formula (I) or a salt thereof, which comprises the following steps:
(i) reaction of 4-fluorobenzaldehyde and 4-amino-2-nitroaniline followed by reduction using standard procedures to produce a compound of formula (II); and
(ii) reacting a compound of formula (II) with diethylcarbonate in the presence of a base to produce a compound of formula (I), or a salt thereof.

In one embodiment of the present invention there is provided a process for the preparation of retigabine, or a salt thereof, which comprises the following steps:
(i) reacting a compound of formula (II) with diethylcarbonate in the presence of a base to produce a compound of formula (I), or a salt thereof; and
(ii) reduction of compound of formula (I) using standard procedures to produce retigabine;
(iii) and optionally preparing a salt thereof.

The present process for the preparation of retigabine allows for a better control of impurity levels and has fewer steps providing better cost of goods.

In one embodiment of the present invention there is provided a process for the preparation of retigabine, or a salt thereof, which comprises the following steps:
(i) reaction of 4-fluorobenzaldehyde and 4-amino-2-nitroaniline followed by reduction using standard procedures to produce a compound of formula (II);
(ii) reacting a compound of formula (II) with diethylcarbonate in the presence of a base to produce a compound of formula (I), or a salt thereof; and
(iii) reduction of compound of formula (I) using standard procedures to produce retigabine;
(iv) and optionally preparing a salt thereof.

The preparation of retigabine from a compound of formula (I) or the preparation of a compound of formula (III) can be carried out using standard procedures for reduction for example using $H_2$ on Platinum (Pt)/Vanadium (V) on carbon or use $H_2$/Raney nickel.

Polymorphic forms A, B and C of retigabine are disclosed in WO98/031663 (U.S. Pat. No. 6,538,151), incorporated in its entirety. Specifically incorporated are the characterising data for the polymorphic forms and their methods of preparation.

The above processes for the preparation of retigabine may further include the preparation of retigabine polymorphic Form A, Form B or Form C, preferably Form A.

In any preparation of retigabine in polymorphic form, a retigabine solvent mixture may be seeded with retigabine of the desired polymorphic form in order to enhance recrystallisation.

In one embodiment of the present invention there is therefore provided a process for the preparation of polymorphic Forms A, B or C of retigabine which comprises the following steps:
(i) reacting a compound of formula (II) with diethylcarbonate with a base to produce a compound of formula (I), or a salt thereof; and
(ii) reduction of compound of formula (I) using standard procedures to produce retigabine; and optionally
(iii) preparing retigabine in polymorphic form optionally including the additional step of seeding the retigabine solvent mixture with retigabine Polymorphic Form A, B or C.

In one embodiment of the present invention there is therefore provided a process for the preparation of polymorphic Forms A, B or C of retigabine which comprises the following steps:
(i) reaction of 4-fluorobenzaldehyde and 4-amino-2-nitroaniline followed by reduction using standard procedures to produce a compound of formula (II);
(ii) reacting a compound of formula (II) with diethylcarbonate with a base to produce a compound of formula (I), or a salt thereof; and
(iii) reduction of compound of formula (I) using standard procedures to produce retigabine; and optionally
(iv) preparing retigabine in polymorphic form optionally including the additional step of seeding the retigabine solvent mixture with retigabine Polymorphic Form A, B or C.

Retigabine and the compounds of formulas (I), (II) and (III), can form acid addition salts thereof. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid.

EXAMPLES

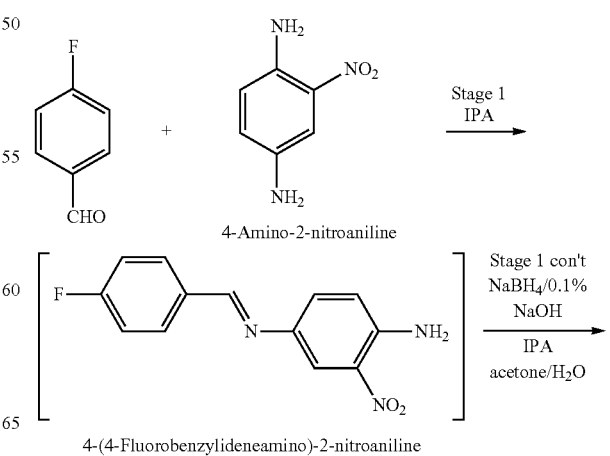

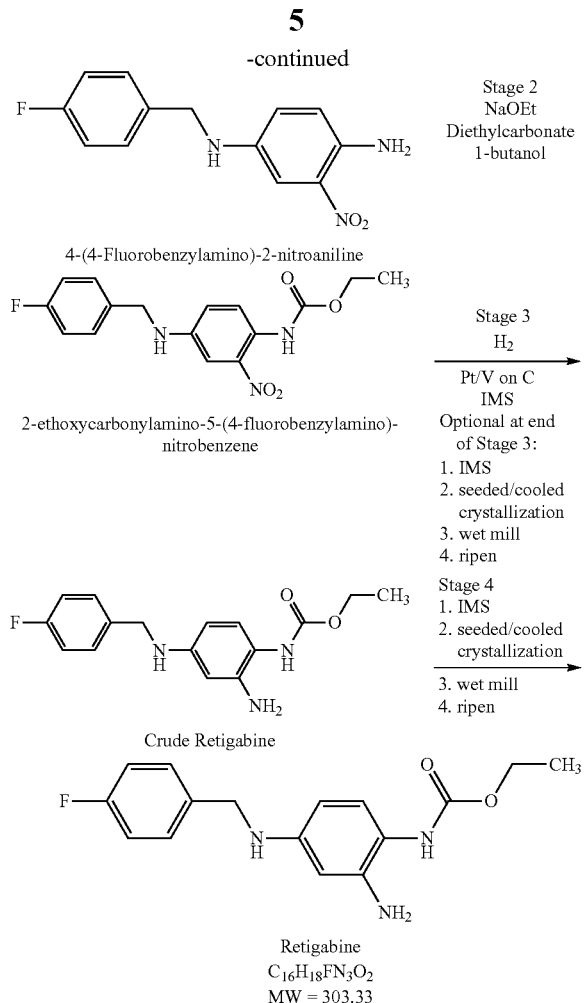

The following abbreviations are defined herein.
IPA—isopropanol or 2-propanol
IMS—Industrial methylated spirit
LOD—limit of detection.

Stage 1—Preparation of 4-(4-fluorobenzylamino)-2-nitroaniline.

4-Amino-2-nitroaniline (1.0 equiv.; 1.0 wt) was dissolved in IPA. The mixture was warmed to 75° C. and 4-fluorobenzaldehyde (1.05 equiv.; 0.285 wt) was added. When formation of imine was complete, a solution of NaBH$_4$ in 0.1% NaOH was added. After complete reduction of the imine at 75° C., water was added to the hot mixture. The mixture was cooled and acetone (0.2 vol) was added. The mixture was cooled to 15° C. and held for at least 30 minutes. Dark brown crystalline solid was collected, washed with water, and dried under vacuum at 50-55° C.

Percent yield range observed: 79-85%

Stage 2—Preparation of 2-ethoxycarbonylamino-5-(4-fluorobenzylamino)-nitrobenzene.

A vessel was charged with 4-(4-fluorobenzylamino)-2-nitroaniline (1.0 equiv.; 1.0 wt), NaOEt (2.0 equiv.; 0.52 wt), and diethylcarbonate (DEC) (7 vol). The heterogeneous mixture was stirred at 20-25° C. for 1.5 h or until complete by HPLC. Acetic acid (2.0 equiv) was charged and the mixture was heated to 40-50° C. H$_2$O and n-BuOH were added to the mixture and the layers were separated. The organic mixture was concentrated under vacuum and n-BuOH was added and distilled via constant volume distillation. The distillation was continued until the desired ratio was obtained. n-BuOH was added and the mixture was adjusted to 60-65° C. to dissolve all solids. The batch temperature was adjusted to 50° C. and seeded with 2-ethoxycarbonylamino-5-(4-fluorobenzylamino)-nitrobenzene. The suspension was stirred at 50° C. and then cooled to 0° C. The solid was filtered and washed with cold n-BuOH. The solid was dried under reduced pressure at 20-40° C.

Percent yield range observed: 80-88%

Stage 3—Preparation of Retigabine

A pressure vessel was charged with 2-ethyoxycarbonylamino-5-(4-fluorobenzylamino)-nitrobenzene, 1 kg (1 wt), and the catalyst, 1% Pt+2% V/C, 50 g (0.05 wt). The vessel was pressure test with nitrogen to 6 barg. The reactor was charged with denatured ethanol, 10 L (10 vol), and the stir rate was set to >450 rpm. The vessel was pressure purged 3 times with nitrogen to 2 barg. The reaction mixture was heated to 50° C. under reactor control. Once an internal temperature of 50° C. was achieved, agitation was discontinued and the reactor purged three times with hydrogen to 2 barg. Following the third hydrogen purge and once the vessel reached 2 barg again, hydrogen flow control was initiated and the agitator activated. The reactor contents were aged for 2 hours. The reaction was heated to 70° C. and stirred for an additional 1 hour at 70° C. Once complete, the reaction mixture was filtered. The filtrate was transfer to a second 20 L vessel. The reactor was rinsed with denatured ethanol, 3 L (3 vol) and heated to >55° C. The rinse was filtered and the solution transferred to the second 20-L vessel. Once the batch temperature dropped below 30° C., a vacuum was established, 100 mbar (solution will boil at ~29° C.), and the solution concentrated to 7.5 L (7.5 vol). The solution was heated to 65° C. and aged until dissolution has occurred. The batch was cooled to 50° C. and seeded with retigabine (API), 5 g (0.005 wt) slurried in denatured ethanol, 20 mL (0.02 vol). After charging the seed, the solution was immediately cooled to 40° C. over 40 minutes, then aged for 60 min. The solution was cooled to 0° C. over 2 hours. The heterogeneous solution was stirred at 0° C. for 1 hour. The batch was milled, isolated and dried. The slurry was transferred to a filter and filtered. The wet cake was transferred to the vacuum oven and dried at 30-40° C. until the LOD indicated <0.5% wt. loss (120° C. for 15 minutes).

Percent yield range observed: 70-90%

Preparation of Polymorph A

A reaction vessel was charged with denatured ethanol (7.0 volumes) and retigabine (1 wt) was added and the heated to 65-75° C. to dissolve, and stirred for 30 minutes. The solution was filtered to clarify with the temperature maintained above 60° C. throughout the filtration process to avoid precipitation of product. The reactor was rinsed and lined with 1 volume of denatured ethanol. After filtration, the filtered solution was reheated to 60-70° C. to ensure dissolution. The solution was cooled to 54-57° C. (55° C.) and temperature of the contents stabilized. The solution was cooled to 48-53° C., and upon reaching the desired temperature range, seeded with 0.5 wt % of Form A wet-milled seeds as a slurry in denatured ethanol (0.02 vol) at room temperature. The seed pot was washed with 0.02 vol denatured ethanol. The slurry was cooled to 30-40° C. (35° C.) and held for 60 minutes. The slurry was then cooled to −5° C. to 5° C. at up to 0.5° C./min.

The particle size was reduced using a wet mill on a reactor recirculation loop. When the target particle size was reached, the batch was heated to about 35° C. and then cooled to 0° C. and held for 30 min up to 24 hours. The slurry was charged to a filter dryer and settled for 30 min. The mother liquors were removed and the filter cake was washed with cold (0° C.

ethanol wash) (2.0 volumes of denatured ethanol). Retigabine was isolated from the filter drier and was placed in appropriate containers.

Percent yield range observed: 85-89%

The invention claimed is:

1. A process for the production of 2-ethoxycarbonylamino-5-(4-fluorobenzylamino)-nitrobenzene (a compound of formula (I)) or a salt thereof:

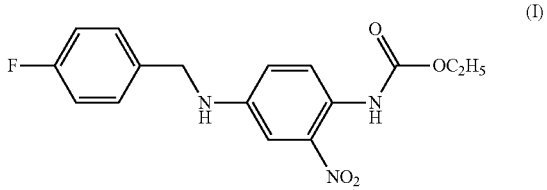 [SMILES: CCOC(=O)Nc1ccc(NCc2ccc(F)cc2)cc1[N+](=O)[O-]]
(I)

which comprises reacting 4-(4-fluorobenzylamino)-2-nitroaniline (the compound of formula (II))

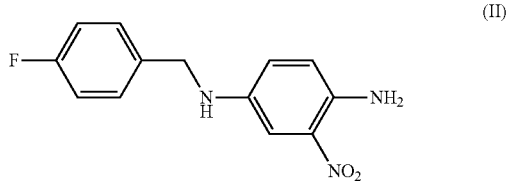 [SMILES: Nc1ccc(NCc2ccc(F)cc2)cc1[N+](=O)[O-]]
(II)

with diethylcarbonate in the presence of a base and optionally preparing a salt thereof.

2. A process as claimed in claim 1 for the preparation of a compound of formula (I) or a salt thereof, which further comprises reaction of 4-fluorobenzaldehyde and 4-amino-2-nitroaniline followed by reduction using standard procedures to produce a compound of formula (II).

3. A process for the preparation of retigabine, or a salt thereof, which comprises the following steps:
   (i) reacting a compound of formula (II) with diethylcarbonate in the presence of a base to produce a compound of formula (I), or a salt thereof; and
   (ii) reduction of compound of formula (I) using standard procedures to produce retigabine;
   (iii) and optionally preparing a salt thereof.

4. A process as claimed in claim 3 for the preparation of retigabine, or a salt thereof, which further comprises reaction of 4-fluorobenzaldehyde and 4-amino-2-nitroaniline followed by reduction using standard procedures to produce a compound of formula (II).

5. A process as claimed in claim 1 wherein the base is selected from sodium ethoxide, sodium hydride, potassium tert-butoxide, n-butyl lithium, potassium hexamethyldisilylazide (KHMDS), cesium carbonate, potassium hydroxide, sodium pentoxide, sodium tert-butoxide, lithium ethoxide, sodium hydroxide, potassium ethoxide, diisopropyl ethyl amine (DIPEA), 1,8-diazabicylco[5.4.0]undec-7-ene (DBU), 1,4-diazabicyclo[2.2.2]octane (DABCO) or lithium tert-butoxide.

6. A process as claimed in claim 1 wherein the base is sodium ethoxide.

7. A process as claimed in claim 1 wherein the base is present in range of 1.8 to 2.2 molar equivalents.

8. A process as claimed in claim 1 wherein the diethyl carbonate is present in the range of 5 to 7 molar equivalents.

9. A process as claimed in claim 1 wherein the reaction is carried out at a temperature in the range 15 to 30° C.

10. A process as claimed in claim 1 wherein the base is neutralized with an acid.

11. A process as claimed in claim 1 wherein the reaction time is in the range 1.5 to 24 hours.

12. A process as claimed in claim 1 wherein the reaction is carried out in a solvent selected from ethanol and isopropanol.

13. A process as claimed in claim 1 which further includes the step of preparing retigabine in polymorphic form, wherein the polymorphic form is Form (A).

14. A process as claimed in claim 3 wherein the base is sodium ethoxide.

15. A process as claimed in claim 3 wherein the base is present in range of 1.8 to 2.2 molar equivalents.

16. A process as claimed in claim 3 wherein the diethyl carbonate is present in the range of 5 to 7 molar equivalents.

17. A process as claimed in claim 3 wherein the reaction is carried out at a temperature in the range 15 to 30° C.

18. A process as claimed in claim 3 wherein the base is neutralized with an acid.

19. A process as claimed in claim 3 wherein the reaction time is in the range 1.5 to 24 hours.

20. A process as claimed in claim 3 wherein the reaction is carried out in a solvent selected from ethanol and isopropanol.

* * * * *